United States Patent [19]

Maki et al.

[11] 4,013,691

[45] Mar. 22, 1977

[54] PROCESS FOR THE SIMULTANEOUS MANUFACTURE OF EPSILON-CAPROLACTONES AND CARBOXYLIC ACIDS

[75] Inventors: Takao Maki, Fujisawa; Kazuyuki Mineta, Yokohama, both of Japan

[73] Assignee: Mitsubishi Chemical Industries Ltd., Tokyo, Japan

[22] Filed: Oct. 8, 1975

[21] Appl. No.: 620,755

[30] Foreign Application Priority Data

Oct. 23, 1974 Japan .................................. 49-122200

[52] U.S. Cl. ............................. 260/343; 260/530 R; 252/428; 252/429 R; 252/431 C; 252/431 N
[51] Int. Cl.$^2$ ........................................ C07D 313/02
[58] Field of Search ........................ 260/343, 530 R

[56] References Cited

UNITED STATES PATENTS

| 3,025,306 | 3/1962 | Guest et al. | 260/343 |
| 3,483,222 | 12/1969 | Sennewald | 260/530 R |
| 3,541,113 | 11/1970 | Hoff | 260/343 |

FOREIGN PATENTS OR APPLICATIONS

| 290,780 | 7/1967 | Australia | 260/343 |
| 1,435,844 | 12/1964 | France | 260/343 |
| 1,411,617 | 10/1963 | France | 260/343 |
| 1,555,113 | 1/1969 | Japan | 260/343 |
| 1,289,523 | 4/1964 | Germany | 260/343.6 |
| 416,330 | 4/1941 | Japan | 260/343 |
| 4,713,506 | 4/1972 | Japan | 260/343 |
| 1,201,673 | 2/1968 | United Kingdom | 260/343 |

*Primary Examiner*—Lewis Gotts
*Assistant Examiner*—D. R. Phillips
*Attorney, Agent, or Firm*—Oblon, Fisher, Spivak, McClelland & Maier

[57] ABSTRACT

A cyclohexanone is oxidized by molecular oxygen in the presence of an aldehyde, a soluble compound of a metal selected from the group consisting of iron, palladium, vanadium, chromium, molybdenum, tungsten and cerium, and a compound which has a heterocyclic ring containing at least one nitrogen atom and which acts as a multidantate ligand, to form an epsilon-caprolactone and a carboxylic acid corresponding to the aldehyde.

14 Claims, No Drawings

PROCESS FOR THE SIMULTANEOUS MANUFACTURE OF EPSILON-CAPROLACTONES AND CARBOXYLIC ACIDS

BACKGROUND OF THE INVENTION

1. Field of the Invention

This invention relates to a process for the simultaneous manufacture of epsilon-caprolactones and carboxylic acids, and more particularly, to the co-oxidation of cyclohexanones and aldehydes to epsilon-caprolactones and carboxylic acids, respectively.

2. Description of the Prior Art

Epsilon-caprolactone is a commercially significant intermediate for formation of a polyester for urethane-polymer manufacture. U.S. Pat. No. 3,025,306 to Guest, issued Mar. 13, 1962, discloses the conversion of cyclohexanones to epsilon-caprolactones by the co-oxidation of the cyclohexanones and aldehydes in the presence of a catalyst such as cobalt, manganese, platinum, palladium, vanadium, ruthenium, zirconium, aluminum, antimony, beryllium and copper. However, this process is characterized by relatively high yields of unwanted by-products such as adipic acid and a relatively low efficiency of the use of the aldehydes, that is, an increased formation of carboxylic acids.

U.S. Pat. No. 3,483,222 to Sennewald, issued Dec. 9, 1969, discloses the preparation of an epsilon-caprolactone by reacting a cyclohexanone with oxygen in the presence of an aldehyde and a soluble iron compound. This process suffers from a relatively low catalyst activity and is not satisfactory for the production of an epsilon-caprolactone from a cyclohexanone.

British Pat. No. 1,009,773 discloses a process for the production of epsilon-caprolactones and carboxylic acids by the co-oxidation of a cyclohexanone together with an aldehyde in the liquid phase with molecular oxygen at a temperature in the range of 50° C to 150° C, the reaction being carried out in the absence of any deliberately provided metallic compounds possessing catalytic activity under the reaction conditions. Also, this reference teaches that when metal compounds are present in low concentrations in the starting materials or when they are introduced upon contact of the reactants and/or the reaction products with the reaction vessel, it is advantageous for the process to be carried out in the presence of sequestering agents such as amino carboxylic acids (EDTA), nitrilo triacetic acids, 1, 2-diamino cyclohexane tetra-acetic acid, hydroxyethyl derivatives of amino triacetic acid, nitrogen-containing heterocyclic compounds (2,2'-bipyridyl, dipicolinic acid), organic phosphates and phosphites, polyphosphates, hydroxy carboxylic acids, 1, 3-diketones, polyamines and Schiff's bases.

Thus, the process of this patent is characterized by the absence of any deliberately provided metallic compounds possessing catalytic activity and the addition of a sequestering agent. However, the aforementioned process poses disadvantages for commercial operation because the low reaction rates of this process, arising from the absence of a catalyst, require higher reaction temperatures which result in lower selectivities of the product epsilon-caprolactones. Moreover, it is to be noted that the preparation of cyclohexanone and butyraldehyde in the presence of metal ions (Mn, Fe, Co, Ni, Zn) and a sequestering agent (2,2'-bipyridyl) is disclosed in Example 11 (Run No. 8) of this patent. One disadvantage of this process is the low selectivity caused by the high reaction temperature and the presence of the harmful heavy metallic ions which catalyze overoxidation reactions. Still a further disadvantage is the use of a large amount of 2,2'-bipyridyl, which lowers the selectivity and makes the process expensive. Furthermore, it is to be noted that there is no indication in this patent that the combination of an iron compound and 2,2'-bipyridyl is a catalyst for the co-oxidation of a cyclohexanone and an aldehyde.

There is a need, therefore, for a more efficient, selective and inexpensive process for the production of epsilon-caprolactones from cyclohexanones.

SUMMARY OF THE INVENTION

Accordingly, it is an object of this invention to provide an inexpensive process for producing caprolactones in high yields and selectivities.

Briefly, this and other objects of this invention, as will hereinafter become clear from the ensuing discussion, have been attained by reacting a cyclohexanone and an aldehyde with oxygen in the presence of a soluble compound of a metal selected from the group consisting of iron, palladium, vanadium, chromium, molybdenum, tungsten and cerium, and a compound which has a heterocyclic ring containing at least one nitrogen atom and which acts as a multidantate ligand.

DESCRIPTION OF THE PREFERRED EMBODIMENTS

The method of this invention is illustrated by the following reaction sequence scheme:

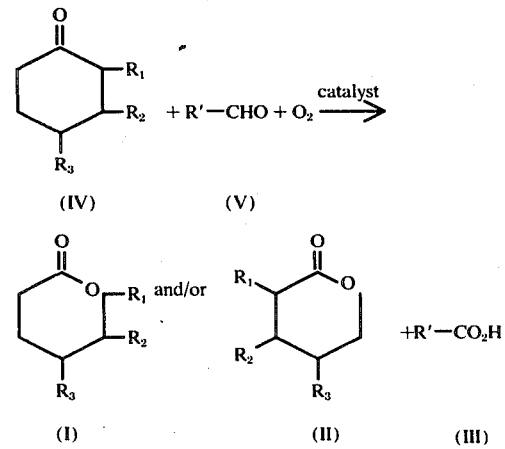

wherein $R_1$ is selected from the group consisting of hydrogen, $C_1$-$C_5$ alkyl and halogen such as F, Cl Br and I. $R_2$ and $R_3$ are selected from the group consisting of hydrogen and $C_1$-$C_5$ alkyl; and R' is selected from the group consisting of hydrogen, $C_1$-$C_{10}$ alkyl, $C_1$-$C_5$ alkenyl, $C_1$-$C_{10}$ formyl-substituted alkyl, phenyl, $C_7$-$C_{12}$ aralkyl, chloromethyl and furyl. Suitable cyclohexanones (IV) for the starting material of this invention include cyclohexanone and substituted cyclohexanones such as 2-methylcyclohexanone, 3-methyl-cyclohexanone, 4-methylcyclohexanone, 2-ethylcyclohexanone and 2-chlorocyclohexanone. Suitable aldehydes (V) include aliphatic aldehydes such as formaldehyde, acetaldehyde, chloroacetaldehyde, propionaldehyde, n-butyraldehyde, isobutyraldehyde, n-hexanal, 2-ethylhexanal, trimethyacetaldehyde, n-hexadecanal, acrolein, crotonaldehyde, glyoxal, adipaldehyde, furfural and phenylacetaldehyde; and aromatic aldehydes such as benzaldehyde and tolualdehyde. Preferred aldehydes are acetaldehyde, propionaldehyde, butyraldehyde, isobutyraldehyde, benzaldehyde and tolualdehyde.

It is to be understood that the particular carboxylic acid produced is dependent upon the aldehyde employed as the starting material. The aldehyde employed will react to yield the corresponding acid. The process can be carried out without using an added diluent or solvent in essence the starting material cyclohexanones and aldehydes and/or the product carboxylic acids being employed as the solvent. Any organic solvent inert to oxidation may also be employed. Suitable such solvents include aliphatic or aromatic hydrocarbons (hexane, cyclohexane, benzene), ketones (acetones, methyl ethyl ketone), esters (ethyl acetate, methyl benzoate), nitriles (acetnitrile, benzonitrile), and the like.

The oxidation of this invention can be conducted with molecular oxygen as the oxidizing agent either as pure oxygen, air, oxygen-enriched air, or the mixtures of oxygen with inert gases such as $CO_2$ and nitrogen. The reaction temperature may vary from −20° C to 150° C. The higher the temperature, the greater will be the conversion of the cyclohexanone- However, higher temperatures increase the yield of undesired by-products such as adipic acid and decrease the selectivity of the epsilon-caprolactone product. Preferably, therefore, the reaction temperature ranges from 10° C to 80° C, more preferably from 20° C to 60° C. The reaction pressure is not critical, but normally ranges from atmospheric pressure to some higher pressure which can be as high as 30 kg/cm².

The characteristic feature of this invention is a new catalyst system comprising a soluble compound of a metal selected from the group consisting of iron, palladium, vanadium, chromium, molybdenum, tungsten and cerium, and a compound which has a heterocyclic ring containing at least one nitrogen atom and which acts as a multidantate ligand. Any soluble compound of the metal can be employed if it is soluble to some extent at temperatures within the operable range, and preferably, is generally completely soluble at the most preferred operating temperatures. Suitable metal compounds include a metal salt of an inorganic acid such as a nitrate, a chloride, a bromide and the like, e.g., Fe(NO)$_3$.9H$_2$O, PdCl$_2$, CrBr$_3$. 6H$_2$O, FeCl$_3$, and the like; a metal salt of an organic acid such as iron naphthenate, an iron salt of a tall-oil fatty acid, iron acetate, palladium acetate, chromium acetate, cerium acetate and the like; a metal complex such as an acetylacetone metal complex such as iron acetylacetonate, palladium acetylacetonate, vanadium acetylacetonate, chromium acetylacetonate, molybdenum acetylacetonate and the like; and a metal carbonyl such as palladium carbonyl compounds cerium carbonyls, tungsten carbonyls, chromium carbonyls and the like.

Preferred compounds which have a heterocyclic ring containing at least one nitrogen atom and which act as a multidantate ligand are represented for example, by the following formula:

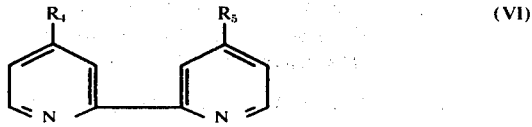

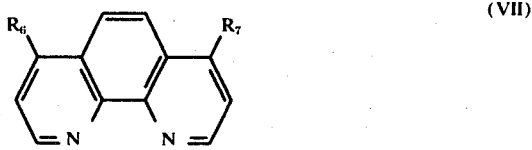

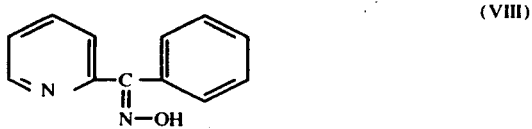

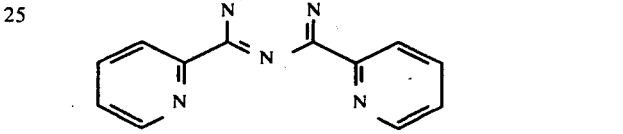

wherein $R_4$ and $R_5$ are independently hydrogen, alkyl, preferably having about 1–4 carbon atoms, or aryl, preferably having about 6–10 carbon atoms, and $R_6$ and $R_7$ are independently hydrogen, alkyl, preferably having about 1–4 carbon atoms, aryl, preferably having about 6–10 carbon atoms, nitro or halogen. Suitable compounds include 2,2'-bipyridyl, 4,4'-dimethyl-2,2'-dipyridyl, 1, 10-phenanthroline, 4, 7-dimethyl-1, 10-phenanthroline, 4, 7-diphenyl-1, 10-phenanthroline, 4-nitrophenanthroline, 4-chlorophenanthroline, (E)-(phenyl 2-pyridyl ketone) oxime and 2,4,6-tris (2-pyridyl)-1,3,5-triazine. Preferred compounds are 2,2'-pyridyl and 1,10-phenanthroline.

Instead of using a separate soluble metal compound and a nitrogen-containing heterocyclic compound, a metal-heterocycle complex can be employed. Suitable complexes include tris (2,2'-bipyridyl) iron perchlorate (Fe(bpy)$_3$(ClO$_4$)$_2$), oxalatobis (2,2'-bipyridyl) iron (Fe(bpy)$_2$(C$_2$O$_4$). 3H$_2$O), dichlorobis (1,10-phenanthroline) iron (Fe(phen)$_2$Cl$_2$), tris (1,10-phenanthroline) iron nitrate (Fe(phen)$_3$(NO$_3$)$_3$), oxobis (2,2'-bipyridyl) vanadium perchlorate (VO(bpy)$_2$(ClO$_4$)$_2$), μ-dichloro (1,10-phenanthroline) palladium (Pd(phen)Cl$_2$), tetracarbonyl (2,2'-bipyridyl) molybdenum (Mo(bpy)(CO)$_4$), trichlorooxo (2,2'-bipyridyl) tungsten (WO(bpy)Cl$_3$), hydroxobis (2,2'-bipyridyl) chromium nitrate (Cr(bpy)$_2$(OH) (NO$_3$)$_2$.3H$_2$O) and the like.

The soluble metal compound can be employed such that the concentration of the metal is in the range of 0.01 to 500 parts per million, preferably 0.1 to 100 parts per million, more preferably 0.5 to 50 parts per million, each based on the total weight of the reaction mixture. The nitrogen-containing heterocyclic compound can be employed such that the concentration thereof is in the range of 0.01 to 200 parts per million based on the weight of the reaction mixture. In addition to increasing the cost of the process, the use of larger amounts of the nitrogen-containing heterocyclic compounds results in an increase in the amount of the undesirable adipic acid obtained, as well as a decrease in the selectivity of the espsilon-caprolacetone product. Preferably, the concentration of the nitrogen-containing heterocyclic compound is in the range of 0.1 to 100 parts per million, more preferably 1 to 50 parts per million on the basis discussed above. The molar ratio of the soluble metal compound to the nitrogen-containing heterocyclic compounds is not critical, but normally in the range of 1: 0.1 – 10. The molar ratio of the cyclohexanones to the aldehydes is also not critical, but it is preferred to employ an excess of the cyclohexanones.

The process of this invention can be carried out by either a batch or a continuous process. The product formed can be recovered by conventional techniques. For example, the reaction mass can be removed as a liquid, and the epsilon-caprolactone and the carboxylic acid can be separated by distillation. Other methods are conventional and are within the knowledge of those skilled in the art. A principal advantage of the process of this invention is that high yields of the epsilon-caprolactones are produced and are accompanied by low yields of the unwanted by-products such as adipic acid and high efficiency in the use of the aldehydes. Having generally described this invention, a more complete understanding can be obtained by reference to certain examples and reference examples which are provided herein for purposes of illustration only and are not intended to be limiting in any manner.

EXAMPLE 1

Into a 500 ml glass flask fitted with a stirrer, an air inlet pipe, a dry ice cooled reflux condenser and a liquid inlet pipe connected to a proportioning pump were charged 156 g (1.59 mole) of cyclohexanone, an amount of the catalyst iron naphthenate to give 1 part per million of iron based on the weight of the total charge of material, and an amount of 2,2'-bipyridyl to effect a concentration of 10 parts per million on the same basis. While the temperature was held at 50° C and air was fed at a rate of 30 l/hr. with stirring, a mixture of 19.0 g (0.432 mole) of acetaldehyde and 80 g (0.82 mole) of cyclohexanone was added through the proportioning pump over a period of 2 hours. Oxygen uptake proceeded smoothly. After the addition of acetaldehyde was complete, the reaction was allowed to continue for an additional 1 hour while feeding air. The reaction product was distilled to remove acetic acid and analyzed by gas phase chromatography. The gas chromatographic analysis indicated that the crude reaction mixture contained 17.8 g (0.157 mole) of epsilon-caprolactone, 2.35 g (0.0161 mole) of adipic acid and 0.0165 equivalent of polymeric caprolactone. Thus, the conversion of cyclohexanone was 7.84% and the selectivities of epsilon-caprolactone, adipic acid and polymeric caprolactone were 82.8%, 8.5% and 8.7%, respectively. The yield of acetic acid was 23.7 g (91.4% based on the amount of acetaldehyde charged).

EXAMPLE 2

Employing o-phenanthroline in place of 2,2'-bipyridyl, Example 1 was repeated. Oxygen uptake proceeded smoothly. Gas chromatographic analysis indicated that the crude reaction mixture contained 17.4 g (0.152 mole) of epsilon-caprolactone, 2.10 g (0.0144 mole) of adipic acid and 0.0142 equivalent of polymeric caprolactone. Thus, the conversion of cyclohexanone was 7.51% and the selectivities of epsilon-caprolactone, adipic acid and polymeric caprolactone were 84.1%, 8.0% and 7.9%, respectively. The yield of acetic acid was 23.8 g (92.0% based on the amount of acetaldehyde charged).

EXAMPLE 3

Employing 31.1 g (0.432 mole) of isobutyraldehyde in place of acetaldehyde, Example 1 was repeated. Oxygen uptake proceeded smoothly. Gas chromatographic analysis indicated that the crude reaction mixture contained 25.9 g (0.227 mole) of epsilon-caprolactone and 0.963 g (0.0066 mole) of adipic acid. Thus, the conversion of cyclohexanone was 9.91% and the selectivities of epsilon-caprolactone and adipic acid were 95.0% and 2.8%, respectively. The yield of isobutyric acid was 32.6 g (85.9% based on the amount of isobutyraldehyde charged).

EXAMPLES 4–9

These examples illustrate the effect of the catalyst concentration employed. In selecting the reaction conditions, particular consideration should be given to the catalyst concentration. Example 1 was repeated, except that the concentrations of iron naphthenate and 2,2'-bipyridyl were varied as indicated in Table 1. The results are shown in Table 1.

TABLE 1

| Example No. | Catalyst Concentration | | Conversion of Cyclohexanone (%) | Selectivity (%)*** | | Yield**** of Acetic Acid |
|---|---|---|---|---|---|---|
| | iron* naphthenate (ppm) | 2,2'-** bipyridyl (ppm) | | epsilon-caprolactone | adipic acid | |
| 1 | 1 | 10 | 7.84 | 82.8 | 8.5 | 91.4 |
| 4 | 1 | 100 | 7.70 | 81.1 | 9.0 | 88.5 |
| 5 | 1 | 250 | 8.01 | 64.5 | 22.2 | 85.3 |
| 6 | 1 | 530 | 9.39 | 53.2 | 26.9 | 85.0 |
| 7 | 0.2 | 10 | 6.27 | 81.2 | 9.3 | 92.0 |
| 8 | 10 | 3 | 7.32 | 79.0 | 8.8 | 90.1 |
| 9 | 50 | 50 | 6.95 | 59.3 | 24.2 | 83.3 |

*parts per million calculated as iron and based on the weight of the total charge of material
**parts per million based on the weight of the total charge of material
***based on the amount of cyclohexanone reacted.
****based on the amount of acetaldehyde charged.

EXAMPLES 10–15

These Examples illustrate the effect of the reaction temperature. In selecting the reaction conditions, particular consideration should be given to the reaction temperature. Example 1 was repeated, except that the reaction temperature and, in some cases, the catalyst concentration were varied as indicated in Table 2. The results are shown in Table 2.

Table 2

| Example NO. | Reaction Temperature C° | Catalyst Concentration iron* naphthenate (ppm) | Catalyst Concentration 2,2'-** bipyridyl (ppm) | Conversion of Cyclohexanone (%) | Selectivity (%)*** epsilon-caprolactone | Selectivity (%)*** adipic acid | Yield**** of Acetic Acid |
|---|---|---|---|---|---|---|---|
| 10 | 28 | 1 | 10 | 5.70 | 77.1 | 9.4 | 89.8 |
| 11 | 40 | 1 | 10 | 7.22 | 84.8 | 8.3 | 89.6 |
| 1 | 50 | 1 | 10 | 7.84 | 82.8 | 8.5 | 91.4 |
| 12 | 60 | 1 | 10 | 6.88 | 72.8 | 10.2 | 85.0 |
| 13 | 75 | 1 | 10 | 9.50 | 60.6 | 14.7 | 72.9 |
| 6 | 50 | 1 | 530 | 9.39 | 54.1 | 21.9 | 84.0 |
| 14 | 75 | 1 | 530 | 11.42 | 53.2 | 26.9 | 85.0 |

*parts per million calculated as iron and based on the weight of the total charge of material
**parts per million based on the weight of the total charge of material
***based on the amount of cyclohexanone reacted
****based on the amount of acetaldehyde charged

EXAMPLES 15-20

Example 1 was repeated, except that the catalyst was varied as indicated in Table 3. The results are shown in Table 3. In Table 3, "acac" stands for acetylacetonate.

Table 3

| Example No. | Catalyst | Catalyst* concentration (ppm) | Conversion of cyclohexanone (%) | Selectivity (%)** Epsilon-caprolactone | Selectivity (%)** Adipic acid | Yield of*** acetic acid |
|---|---|---|---|---|---|---|
| 15 | Cr(acac)₃ | 5 | 3.41 | 86.1 | 6.4 | 72.7 |
|  | 2,2'-bipyridyl | 50 |  |  |  |  |
| 16 | Cerium acetate | 5 | 2.92 | 81.1 | 9.1 | 75.9 |
|  | 2,2'-bipyridyl | 100 |  |  |  |  |
| 17 | VO(acac)₂ | 5 | 4.22 | 87.8 | 6.4 | 77.1 |
|  | 2,2'-bipyridyl | 50 |  |  |  |  |
| 18 | Palladium acetate | 10 | 4.01 | 87.0 | 7.7 | 73.5 |
|  | 2,2'-bipyridyl | 50 |  |  |  |  |
| 19 | MoO₂(acac)₂ | 10 | 4.83 | 85.8 | 4.4 | 52.2 |
|  | 2,2'-bipyridyl | 50 |  |  |  |  |
| 20 | W(CO)₆ | 10 | 4.12 | 87.0 | 4.0 | 53.3 |
|  | 2,2'-bipyridyl | 50 |  |  |  |  |

*The concentration of the metal compounds is calculated based on the metal contained and based on the weight of the total charge of material. The concentration of the nitrogen-containing compounds is based on the weight of the total charge of material.
**based on the amount of cyclohexanone reacted
***based on the amount of acetaldehyde charged

EXAMPLE 21

Employing 5.6 mg of oxalatobis (2,2'-bipyridyl) iron (Fe(bpy)₂ (C₂O₄)3H₂O) in place of iron naphthenate and 2,2'-bipyridyl, Example 1 was repeated. Oxalatobis (2,2'-bipyridyl) iron was prepared according to the method of E. Konig and K. Madeja (Inorg. Chem., 7 1848 (1968)). Gas chromatographic analysis indicated that the conversion of cyclohexanone was 5.38%, and that the selectivities of epsilon-caprolactone and adipic acid were 74.1% and 8.8%, respectively.

REFERENCE EXAMPLE 1

Example 1 was repeated, except that 2,2'-bipyridyl was not added. The rate of oxygen uptake was very low and soon the reaction stopped completely. Gas chromatographic analysis indicated that the yield of acetic acid was 31.3%, and that the conversion of cyclohexanone was only 1.86%.

REFERENCE EXAMPLE 2

Example 1 was repeated, except that iron naphthenate and 2,2'-bipyridyl were not added, and that ferric acetate was added in an amount in order to effect a concentration of 1 part per million (calculated as iron) based on the weight of the total charge of material. The rate of oxygen uptake was very low and soon the reaction stopped. Gas chromatographic analysis indicated that the yield of acetic acid was 18.4%, and that the conversion of cyclohexanone was 1.50%. When 10 ppm of 2,2'-bipyridyl were present in the system, the reaction proceeded smoothly, and the results were substantially identical with those of Example 1. It is important to emphasize that the absence of 2,2'-bipyridyl results in a considerable reduction in the conversion of cyclohexanone as compared with the results of the reaction carried out in the presence of 2,2'-bipyridyl.

REFERENCE EXAMPLE 3

Example 1 was repeated, except that 2,2'-bipyridyl was not added. The rate of oxygen uptake was very low. The yield of acetic acid was 37.4% (based on the amount of acetaldehyde charged).

REFERENCE EXAMPLE 4

This reference example illustrates the necessity of the presence of the catalyst. Example 1 was repeated, except that iron naphthenate and 2,2'-bipyridyl were not added, and that the reaction temperature was raised to 75° C so as to increase the reaction rate. The rate of oxygen uptake was very low. Gas chromatographic analysis indicated that the conversion of cyclohexanone was 1.89%, and that the selectivities of epsilon-caprolactone and adipic acid were 63.5% and 7.2%, respectively. The yield of acetic acid was 26.6% (based on the amount of acetaldehyde charged). It will be apparent from the results of this Reference Example that the use of the catalyst system comprising the soluble metal compound and the nitrogen-containing heterocyclic compound allows the use of lower reaction temperatures, improves the selectivity of the epsilon-caprolactone and results in a surprising reduction in the formation of by-products when compared with the results when the process is carried out in the absence of the catalyst.

REFERENCE EXAMPLE 5-14

These Reference Examples illustrate the ineffectiveness of the catalyst systems indicated in Table 4. Example 1 was repeated, except that the catalyst and reaction conditions were varied as indicated in Table 4.

REFERENCE EXAMPLE 15

This Reference Example and Reference Example 16 illustrate the insufficiency of a catalyst consisting of Mn, Fe, Co, Ni, Zn and 2,2'-bipyridyl as disclosed in Example 11 of British Pat. No. 1,009,773. Example 1 was repeated except that approximate amounts of zinc acetylacetonate, nickel naphthenate, manganese naphthenate and cobalt naphthenate were charged to give 0.5 ppm Zn, 0.3 ppm Ni, 0.5 ppm Mn and 1.3 ppm Co, respectively, based on the weight of the total charge of material. The oxygen uptake proceeded smoothly. Gas chromatographic analysis indicated that the conversion of cyclohexanone was 9.51%, and that the selectivities of epsilon-caprolactone and adipic acid were 52.1% and 26.8%, respectively. The yield of acetic acid was 80.7%.

REFERENCE EXAMPLE 16

Reference Example 15 was repeated, except that the concentration of iron and 2,2'-bipyridyl were 0.7 ppm and 530 ppm, respectively. The oxygen uptake proceeded smoothly. Gas chromatographic analysis indicated that the conversion of cyclohexanone was Table 4

| Reference ex. No. | Reaction temperature °C | Catalyst | Catalyst* concentration (ppm) | Moles cyclohexanone charged | Solvent | Oxygen uptake | Yield** of acetic acid |
|---|---|---|---|---|---|---|---|
| 5 | 50 | Copper acetylacetonate 2,2'-bipyridyl | 5 10 | 2.42 | none | none | *** |
| 6 | 50 | Cu(NO$_3$)$_2$ 2,2'-bipyridyl | 5 50 | 0.878 | Acetic Acid 3 mole | none | *** |
| 7 | 30 | Cu(NO$_3$)$_3$ 2,2-bipyridyl | 50 600 | 0.878 | none | poor →stop | *** |
| 8 | 50 | Zinc acetylacetonate 2,2'-bipyridyl | 50 100 | 2.42 | none | none | *** |
| 9 | 40 | iron naphthenate [structure: bis-salicylaldimine ligand with CH=N—CH—CH—N=CH bridge and two OH-substituted phenyl rings] | 1 10 | 2.42 | none | poor →stop | 40.5% |
| 10 | 50 | iron naphthenate [structure: pyridine-2,6-dicarboxylic acid, CO$_2$H groups] | 1 20 | 2.42 | none | almost none | 11.0% |
| 11 | 40 | iron naphthenate [structure: pyridine-2-carboxylic acid] | 1 10 | 2.42 | none | poor →stop | *** |
| 12 | 40 | iron acetylacetonate [structure: pyridine-2,5-dicarboxylic acid] | 5 10 | 2.42 | none | poor →stop | *** |
| 13 | 40 | iron naphthenate EDTA disodium salt | 1 10 | 2.42 | none | poor | 31.2% |
| 14 | 50 | palladium acetate | 10 | 2.42 | none | poor | 36.2% |

*The concentration of the metal compound is calculated based on the metal content and based on the weight of the total charge of material. The concentration of the nitrogen-containing compound or sequestering agent is based on the weight of the total charge of material.
**based on the amount of acetaldehyde charged
***The yield of acetic acid was not determined.

10.13%, and that the selectivities of epsilon-caprolactone and adipic acid were 50.1% and 27.0%, respectively. The yield of acetic acid was 81.1%.

The advantages of this invention can be readily ascertained when the efficiencies of the preferred catalyst systems of this invention as illustrated in the Examples are compared with the prior art catalyst systems of the Reference Examples, in which (1) the catalyst is absent (Reference Example 4), (2) the nitrogen-containing heterocyclic compound is absent (Reference Examples 1–3), (3) a large amount of 2,2'-bipyridyl is employed (Reference Example 15), or (4) a harmful metal is present (Reference Examples 15–16).

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. In a process for the simultaneous manufacture of epsilon-caprolactones of formula (1),

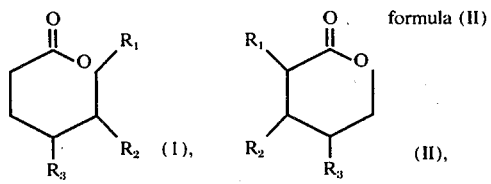

or mixtures thereof, wherein $R_1$ is selected from the group consisting of hydrogen, $C_1$–$C_5$ alkyl and halogen; and $R_2$ and $R_3$ are selected from the group consisting of hydrogen and $C_1$–$C_5$ alkyl, and of carboxylic acids of formula (III), $R'$—$CO_2H$ (III), wherein $R'$ is selected from the group consisting of hydrogen, $C_1$–$C_{10}$ alkyl, $C_1$–$C_5$ alkenyl, $C_1$–$C_{10}$ formyl - substituted alkyl, phenyl, $C_7$–$C_{12}$ aralkyl, chloromethyl and furyl, by oxidizing a cyclohexanone of formula (IV),

wherein $R_1$, $R_2$ and $R_3$ are as defined above, and an aldehyde of formula (V), $$R' - CHO, \qquad (V)$$

wherein $R'$ is as defined above, with molecular oxygen, the improvement which comprises effecting said oxidation in the presence of a soluble compound of a metal selected from the group consisting of iron, palladium, vanadium, chromium, molybdenum, tungsten and cerium, and a compound which has a heterocyclic ring containing at least one nitrogen atom and which acts as a multidantate ligand.1 selected from the group consisting of:

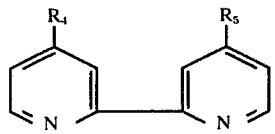

wherein $R_4$ and $R_5$ are selected from the group consisting of hydrogen, $C_1$–$C_4$ alkyl and $C_6$–$C_{10}$ aryl;

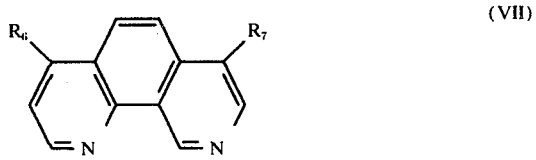

wherein $R_6$ and $R_7$ are selected from the group consisting of hydrogen $C_1$–$C_4$ alkyl, $C_6$–$C_{10}$ aryl, nitro and halogen;

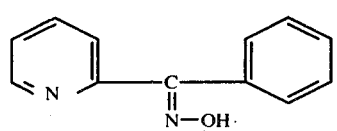

and

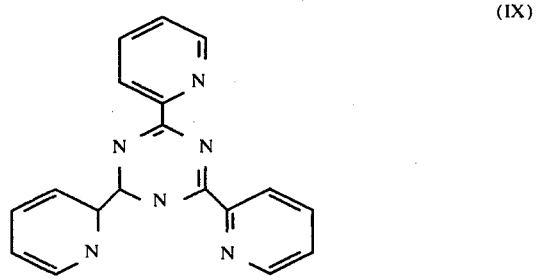

2. The process of claim 1 wherein the cyclohexanone is selected from the group consisting of cyclohexanone, 2-methylcyclohexanone, 3-methylcyclohexanone, 4-methylcyclohexanone, 2-ethylcyclohexanone and 2-chlorocyclohexanone.

3. The process of claim 1 wherein the aldehyde is selected from the group consisting of formaldehyde, acetaldehyde, chloroacetaldehyde, propionaldehyde, n-butyraldehyde, isobutyraldehyde, n-hexanal, 2-ethylhexanal, trimethylacetaldehyde, n-hexadecanal, acrolein, crotonaldehyde, glyoxal, adipaldehyde, furfural, phenylacetaldehyde, benzaldehyde and tolualdehyde.

4. The process of claim 3 wherein the aldehyde is selected from the group consisting of acetaldehyde, propionaldehyde, n-butyraldehyde, isobutyraldehyde, benzaldehyde and tolualdehyde.

5. The process of claim 1 wherein the soluble metal compound is selected from the group consisting of a metal salt of an inorganic acid, a metal salt of an organic acid, an acetylacetone metal complex and a metal carbonyl.

6. The process of claim 1 wherein said compound is 2,2'-bipyridyl or 1, 10-phenanthroline.

7. The process of claim 1 wherein the concentration of the soluble metal compound is in the range of 0.1 to 50 parts per million calculated based on the metal content and based on the weight of the reaction mixture.

8. The process of claim 1 wherein the concentration of the nitrogen-containing heterocyclic compound is in the range of 0.1 to 100 parts per million based on the weight of the reaction mixture.

9. The process of claim 1 wherein said process is carried out at a temperature in the range of 20° C to 60° C.

10. The process of claim 1 wherein a metal-heterocycle complex is employed instead of the separate soluble metal compound and nitrogen-containing heterocyclic compound.

11. The process of claim 1 wherein the cyclohexanone and an aldehyde selected from the group consisting of acetaldehyde propionaldehyde, n-butyraldehyde, isobutyraldehyde, benzaldehyde and tolualdehyde are oxidized at a temperature in the range of 20° C to 60° C in the presence of a soluble compound of a metal selected from the group consisting of iron, palladium vanadium, chromium, molybdenum, tungsten and cerium, and a nitrogen-containing heterocyclic compound selected from the group consisting of 2,2'-bipyridyl and 1,10-phenanthroline, the concentration of the soluble metal compound being in the range of 0.1 to 50 parts per million calculated based on the metal content and based on the weight of the reaction mixture, and the concentration of the nitrogen-containing heterocyclic compound being in the range of 0.1 to 100 parts per million based on the weight of the reaction mixture.

12. The process of claim 1 wherein the oxidation is effected in the presence of a soluble compound of a metal selected from the group consisting of palladium, vanadium, chromium, molybdenum, tungsten and cerium.

13. The process of claim 1 wherein the oxidation is effected in the presence of a soluble iron compound.

14. The process of claim 1 wherein the oxidation is effected in the presence of a soluble compound selected from the group consisting of chromium, molybdenum, tungsten and cerium.

* * * * *